(12) United States Patent
Lo

(10) Patent No.: US 7,950,163 B2
(45) Date of Patent: May 31, 2011

(54) FOOT TYPE AND PLANTAR PRESSURE MEASURING DEVICE

(76) Inventor: Ming-Jor Lo, Taipei (TW)

( * ) Notice: Subject to any disclaimer, the term of this patent is extended or adjusted under 35 U.S.C. 154(b) by 0 days.

(21) Appl. No.: 12/649,626

(22) Filed: Dec. 30, 2009

(65) Prior Publication Data

US 2010/0293799 A1 Nov. 25, 2010

(51) Int. Cl.
*A61B 5/103* (2006.01)
*G01B 21/20* (2006.01)
(52) U.S. Cl. ........................ 33/515; 73/379.01
(58) Field of Classification Search .................... 33/515; 73/379.01
See application file for complete search history.

(56) References Cited

U.S. PATENT DOCUMENTS

| | | | | |
|---|---|---|---|---|
| 2,325,490 | A * | 7/1943 | Elftman | 353/80 |
| 5,390,680 | A * | 2/1995 | Brenner | 600/592 |
| 5,539,020 | A * | 7/1996 | Bracken et al. | 523/212 |
| 5,678,566 | A * | 10/1997 | Dribbon | 600/592 |
| 6,651,349 | B2 * | 11/2003 | Coplon et al. | 33/3 A |
| 6,892,574 | B1 * | 5/2005 | Lo | 73/379.01 |
| 7,346,998 | B2 * | 3/2008 | Tadin et al. | 33/515 |
| 7,549,232 | B2 * | 6/2009 | Tadin | 33/515 |
| 2005/0171456 | A1 * | 8/2005 | Hirschman et al. | 600/592 |

* cited by examiner

*Primary Examiner* — Christopher W Fulton

(57) ABSTRACT

A foot type and plantar pressure measuring device is provided. The device includes a color pad and a foggy film on the color pad. The device further includes a mesh pad on the foggy film and/or a resilient pad under the color pad, the resilient pad having protrusions. When a patient stands still on the device for a few seconds and then steps off, the patient's foot type and plantar pressure is shown by color pattern displayed on surface areas of the foggy film. The color pattern corresponds to the plantar pressure exerted on the device, and tones of the color pattern represent the plantar pressure exerted on the surface areas.

15 Claims, 4 Drawing Sheets

FOOT TYPE AND PLANTAR PRESSURE MEASURING DEVICE

CROSS REFERENCE

| | | |
|---|---|---|
| 6,231,527 | May 15, 2001 | Nicholas |

BACKGROUND OF THE INVENTION

1. Field of the Invention

The present invention relates to a foot type and plantar pressure measuring structure. It is a display-via-contact mechanism. It can be used to investigate foot type and plantar pressure distribution. Foot type and plantar pressure are presented via color pattern displayed in different tone, size and location from the still standing style measurement.

2. Description of Related Art

Feet play an important role for supporting our body weight, reducing the force exerted on our lower limbs and related joints, absorbing vibrations, buffering impacts and controlling the balance of our body when our body is in contact with the ground. Such functions can be carried out mainly by the coordination of our tissues including bones, ligaments and muscles, etc.

In general, at least 80% of us have foot problems. Injuries to our ankles or feet change the dynamics of our gait and further produce pressure on the joints of our lower limbs, and thus may cause pathological changes to our joints. However, such problems usually can be corrected by appropriate assessments, treatments and medical care.

Current plantar pressure measurement can be divided in to two kinds, including dynamic gate assessment and free still standing assessment. The cost of dynamic gate assessment is very high. It requires plantar pressure measurement system including sensors and computer equipment operated by professionals to conduct the assessment. The same system can also be use for free still standing assessment.

On the other hand, one of the commonly used free standing assessment methods, so called Harris Mat, utilizes an ink contact-printing mechanism with printing patterns of squares and fine grids engraved in different level of depth. When a patient steps over the back side of the patterned printing pad, the pre-inked printing pad is therefore forced to be in direct contact with the printing paper underneath. The greater the force exerted over the printing pad, the more the patterns of fine grids from deeper area gets printed over the paper. The printed pattern is used to investigate the patient's plantar pressure.

The ink contact-printing method provides a low cost plantar pressure measurement. It relies on paper and inks as the output media. Therefore it is subject to the supplies of paper and quality of printing which depends on proper supply of inks on the printing surface. It requires repeat proper inking to maintain quality printing. Over inking causes a smeared print and must be redone. When conducting group diagnostic or mass screening, one must keep inking the printing surface properly, in addition to continuously replacing the printing paper. Both processes are none-value-added and cumbersome, and sometimes the inking process can be messy.

We therefore, identified the above needs for improvements. As an inventor with years of experience in this field coupled with a few approved patents, I intend to conduct research and further improve this method in order to reach the goal of a low cost and easy to use paperless and inkless solution that will also be environmental friendly. After tireless research countless experiments, we finally reached an improved structure.

For the device structure of this invention, style, goal and spirit, please refer to following figures and examples that will provide a complete understanding of the invention.

For a better understanding of the structure, style, and goal of the invention, please refer to the following figures and examples.

BRIEF SUMMARY OF THE INVENTION

The present invention is a foot type and plantar pressure measuring structure which is comprised of a meshed pad, a semi-transparent thin film, a color pad, and a pad with resilient protrusions being stacked in the order described, such that when a patient stands on top for few seconds and steps off, the invention shows the patient's foot type and plantar pressure by the color pattern displayed. Colored areas that are generated come from the direct stick-on contact between the semi-transparent thin film and the color pad with interaction from the pad with resilient protrusions. The location of contact color, size of contact color, and tone of contact color displayed from this device can be used to determine foot type and plantar pressure distribution. The meshed pad can be an optional item to use. Without using the meshed pad, foot type and pressure are displayed without the pattern of mesh.

The tone of color displayed, size of contact area displayed, and locations of contact displayed are the response of a combined output of each layer from the structure to the various pressures from plantar area exerted to the measuring area. Such response from this measuring device can be used to evaluate foot type and plantar pressure distribution. This information can be used for the purchase or fabrication of orthotics shoes or insoles. Foot type and plantar pressure distribution can be obtained visually by this invention which is a low cost, easy to operate system without the need of any paper, ink or electricity.

NAME OF PARTS AND SYMBOLS USED IN FIGURES

Figure 1:
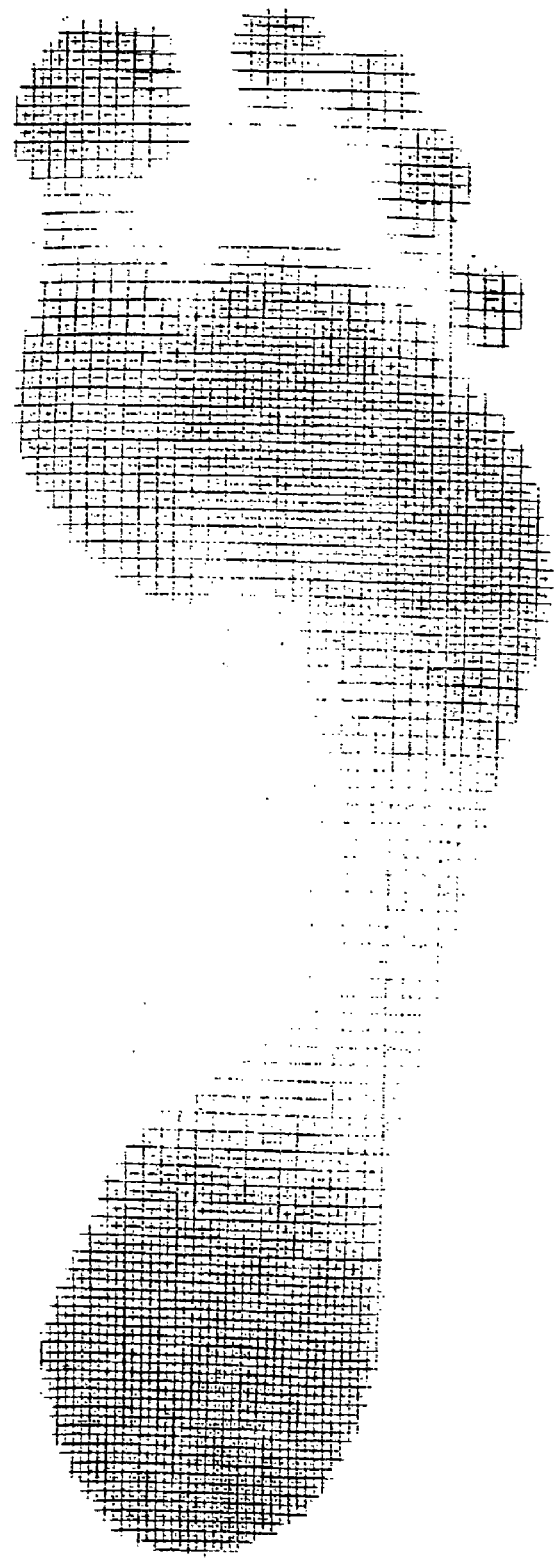
FIG. 1 is an illustrative view of the popularly known square-and-grid printout showing the distribution of plantar pressure.

10 mesh pad
101 holes from mesh pad
20 thin film
30 color pad
40 pad with resilient protrusions
401 resilient protrusions

DETAILED DESCRIPTION OF EMBODIMENTS

Example 1

Figure 2:
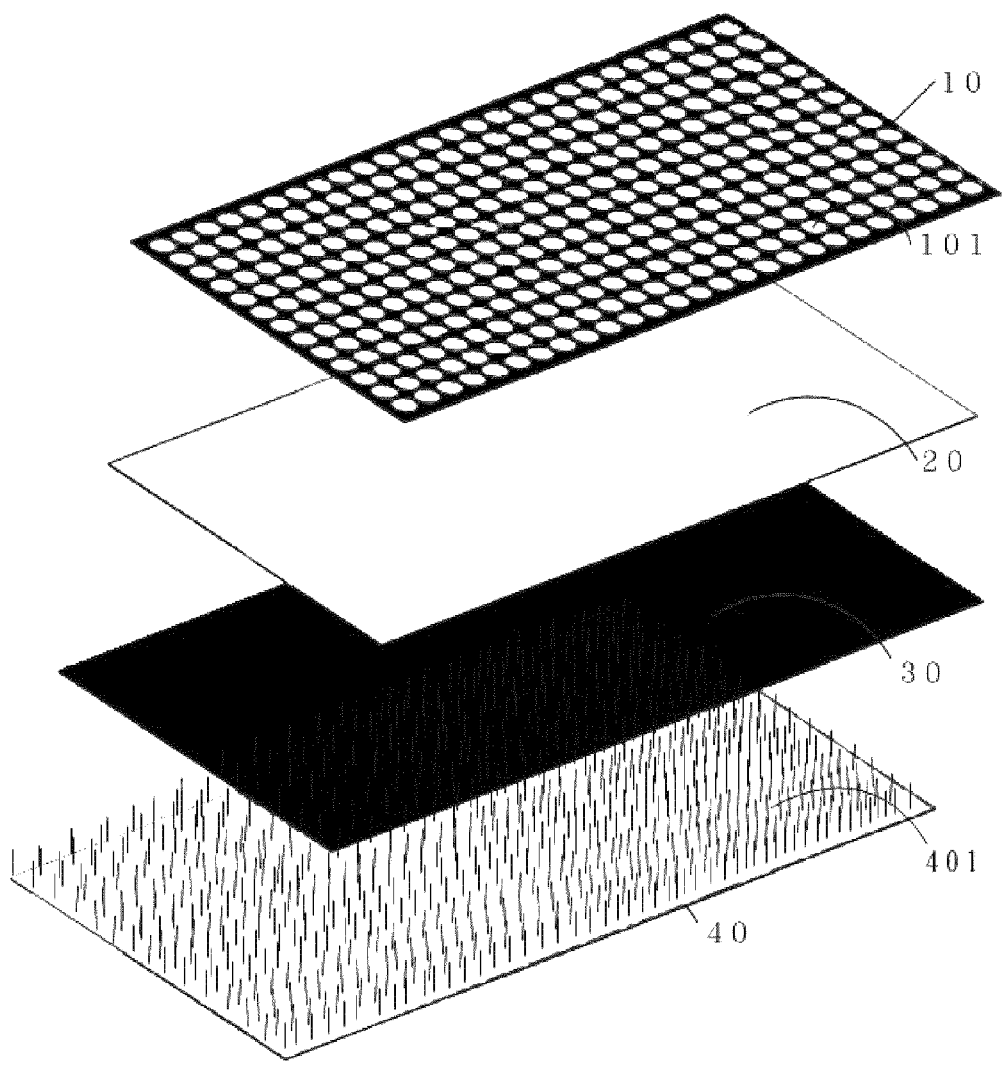
FIG. 2 is a perspective view of the first embodiment of the improved foot type and plantar pressure testing structure.

FIG. 2 is the perspective view of the first example of the invention of foot type and plantar pressure measuring structure. It includes:

A single or multiple layered meshed pad 10 with an array of holes 101 in a circle or polygonal in shape.

A foggy or semi-transparent thin film 20 that is a soft flexible film with a sticky surface property A soft and flexible color pad or plate 30 constructed with color and sticky material; darker color is preferred for best performance.

A pad with resilient protrusions 40, being a firm or semi-rigid pad and having a plurality of protrusions 401 thereon, wherein the shape, size, coarseness, and density of distribution of said protrusions vary as needed.

The above mentioned mesh pad 10, thin film 20, color pad 30 and pad with resilient protrusions 40 are stacked up together in such order shown. If needed, the measuring device can be placed inside a box for easy assembly and disassembly.

Figure 3:
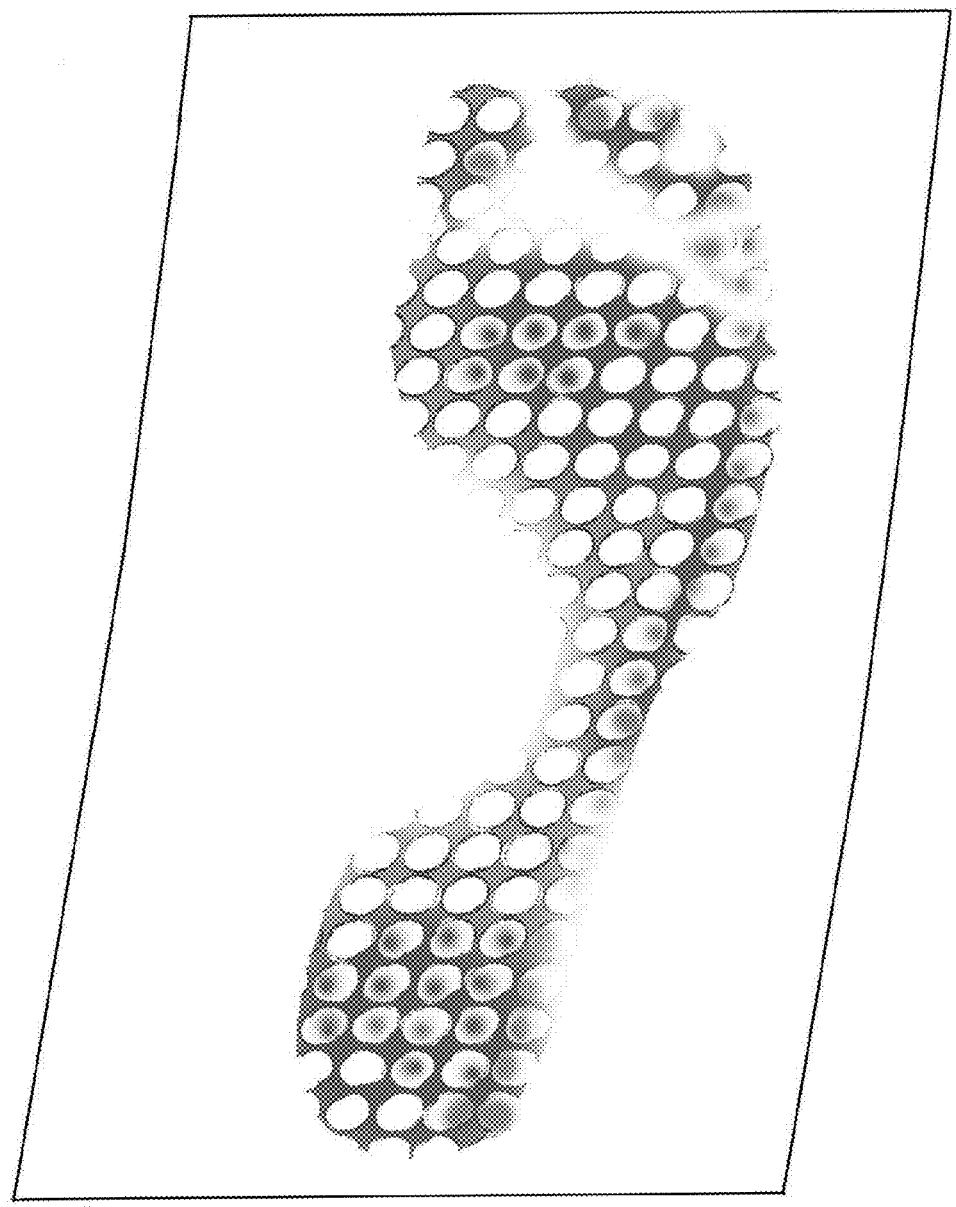
FIG. 3 is from this invention, an illustrative view of the resulting output of the foot type and plantar pressure testing structure.
Figure 4:
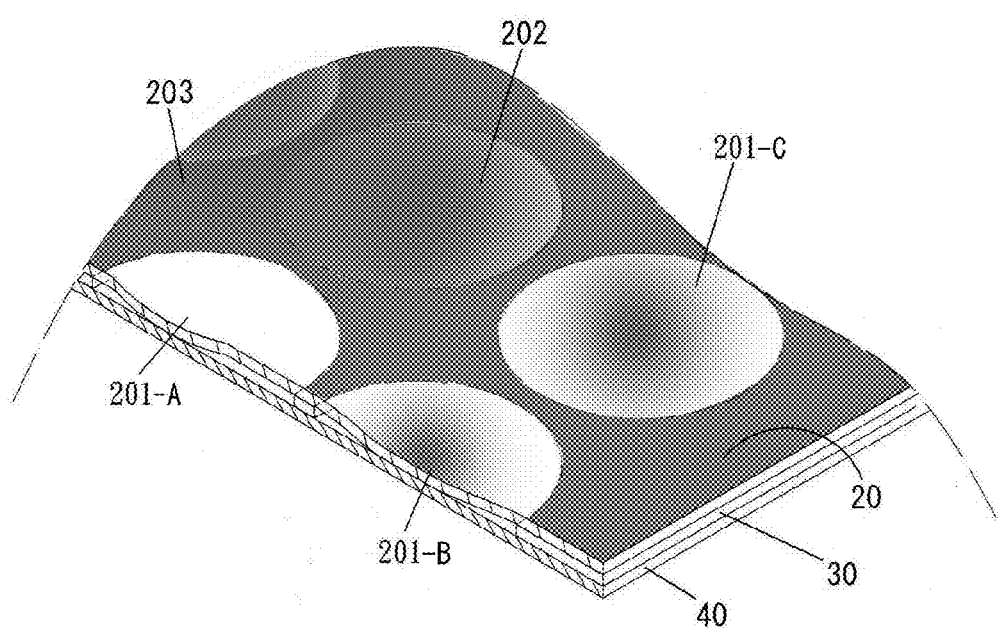
FIG. 4 is an example of measuring results showing different tone of color that indicates different plantar pressure in the respective locations.

As shown in FIG. 2, the mesh pad 10, thin film 20, color pad 30 and pad with resilient protrusions 40 are assembled in the order shown. A patient can stand still on top of the assembly for a few seconds and step off. One can then lift or remove the mesh pad 10 from the assembly and, without the use of a computer, ink, or any paper, receive the measurement results by visual inspection directly, as shown in FIG. 3. The mesh pad 10 and film 20 are pressed down due to plantar pressure from top. When film 20 gets pushed down and becomes in contact with color pad 30 which was lightly pushed back up by the reactive force from the pad with resilient protrusions 40, film 20 and color pad 30 begin to stick together by contact and film 20 starts to show color. The size of the colored area and tone of the color are a function of pressure exerted to the area. FIG. 4 shows examples of results. 201-A shows a smaller pressure, 201-B shows a medium pressure and 201-C shows a larger pressure. Shown in 202, the circle is filled with a solid color, indicating the maximum pressure this device can display. In the locations where 202 and 203 are both filled with a solid color, the area is the peak pressure area or one of the peak pressure areas.

After the process in example 1 has been performed, one can lift or remove the film 20 and all colored areas from contact between film 20 and color pad 30 will disappear automatically. The device is ready to take measurements again by replacing the mesh pad 10 and film 20 in the same order described above. The device can also be used to display foot type and plantar pressure without the use of mashed pad 10. In such case, the displayed pattern will not have the imprints from the mesh.

Therefore, this invention can be used to measure foot type and plantar pressure without the use of paper, ink, or electricity, which is not seen by any other patent applications.

What the invention claimed is:

1. A foot type and plantar pressure measuring device, comprising:
   a soft, flexible color pad made of a sticky material; and
   a semi-transparent film on the color pad;
   wherein surface areas of the semi-transparent film display colors in response to a pressure exerted on the semi-transparent film and the color pad, and
   wherein tones of the colors are associated with the pressure exerted on the surface areas.

2. The device of claim 1, further comprising a meshed pad having a plurality of holes, the meshed pad being placed on the semi-transparent film.

3. The device of claim 2, wherein at least one of the holes are of a circular shape, a circle-like shape, or a polygonal shape.

4. The device of claim 1, wherein the semi-transparent film comprises a foggy film.

5. The device of claim 1, wherein the color pad is of a dark color.

6. The device of claim 5, wherein the dark color comprises any color from gray to black.

7. The device of claim 1, further comprising a resilient pad formed under the color pad.

8. The device of claim 7, wherein the resilient pad includes a plurality of protrusions for exerting a reactive force on the color pad.

9. A device for measuring plantar pressure, comprising:
   a resilient pad including a plurality of protrusions;
   a color pad on the resilient pad; and
   a semi-transparent film on the color pad, wherein surface areas of the semi-transparent film display colors in response to a pressure exerted on the semi-transparent film and the color pad.

10. The device of claim 9, wherein the protrusions contact the color pad.

11. The device of claim 9, wherein tones of the colors are associated with the pressure exerted on the surface areas.

12. The device of claim 9, further comprising a meshed pad on the semi-transparent film, the meshed pad having a plurality of holes.

13. A device for measuring plantar pressure, comprising:
   a resilient pad including a plurality of protrusions;
   a color pad on the resilient pad, the color pad being made of a sticky material;
   a light transmitting film on the color pad; and
   a meshed pad on the light transmitting film, the meshed pad having a plurality of holes.

14. The device of claim 13, wherein at least one of the holes are of a circular shape, a circle-like shape, or a polygonal shape.

15. The device of claim 13, wherein the protrusions contact the color pad.

* * * * *